(12) United States Patent
Brenner et al.

(10) Patent No.: US 6,963,444 B2
(45) Date of Patent: Nov. 8, 2005

(54) STAND ARRANGEMENT FOR A MEDICAL-OPTICAL INSTRUMENT

(75) Inventors: Roland Brenner, Wallhausen (DE); Klaus Abele, Schwäbisch Gmünd (DE)

(73) Assignee: Carl-Zeiss-Stiftung, Heidenheim (DE)

( * ) Notice: Subject to any disclaimer, the term of this patent is extended or adjusted under 35 U.S.C. 154(b) by 0 days.

(21) Appl. No.: 10/788,357

(22) Filed: Mar. 1, 2004

(65) Prior Publication Data

US 2004/0190131 A1   Sep. 30, 2004

(30) Foreign Application Priority Data

Mar. 7, 2003   (DE) ................................ 103 10 459

(51) Int. Cl.⁷ ............................................. G02B 21/00
(52) U.S. Cl. ............... 359/384; 248/123.2; 248/281.11
(58) Field of Search ................................ 359/368, 382, 359/384; 248/123.11, 123.2, 124.1, 124.2, 248/280.11, 281.11

(56) References Cited

U.S. PATENT DOCUMENTS

| 5,528,417 A   | 6/1996 | Nakamura ................... 359/384 |
| 5,651,718 A * | 7/1997 | Nakamura ............... 248/123.2 |
| 6,050,530 A * | 4/2000 | Nakamura ............... 248/123.2 |
| 6,186,023 B1* | 2/2001 | Nakamura et al. ....... 74/490.01 |

* cited by examiner

*Primary Examiner*—Mark A. Robinson
(74) *Attorney, Agent, or Firm*—Walter Ottesen

(57) ABSTRACT

The invention relates to a stand arrangement (100) for a medical-optical instrument. The stand arrangement includes a first link (104) which is pivotally supported on a holding unit (101) by a first rotational joint. The stand arrangement (100) further includes a second link (106) which is rotatably connected to the first link (104) via a second rotational joint (105). A take-up unit (109) for medical-optical equipment is held in a forward section (107, 108) of the second link (106) by a third rotational joint. The take-up unit (109) includes a front link (111) which, in turn, is connected via a third link (112) and a fourth link (113) to the second rotational joint (105). The holding unit (101) and the fourth link (113) are coupled with the aid of a toothed gear unit (118) in such a manner that the orientation of the front link (111) does not change with the movement of the first link (104).

14 Claims, 6 Drawing Sheets

STAND ARRANGEMENT FOR A MEDICAL-OPTICAL INSTRUMENT

CROSS REFERENCE TO RELATED APPLICATION

This application claims priority of German patent application no. 103 10 459.3, filed Mar. 7, 2003, the entire content of which is incorporated herein by reference.

FIELD OF THE INVENTION

The invention relates to a stand arrangement for a medical-optical instrument having a first link which is pivotally journalled on a holding unit by a first rotational joint and having a second link which is rotatably connected via a second rotational joint to the first link and which carries a take-up unit for medical-optical equipment in a forward section via a third rotational joint. The take-up unit includes a front link which is connected via a third link and a fourth link to the second rotational joint.

BACKGROUND OF THE INVENTION

A stand apparatus of the above kind is disclosed in U.S. Pat. No. 5,528,417. There, a stand apparatus for a medical-optical instrument is described which carries medical-optical equipment on a holding unit by means of a first parallel linkage pair and a second parallel linkage pair. The medical-optical equipment is accommodated on a front link of a parallel linkage pair which is connected to a crank-shaped clamp joint element via a third linkage unit. This clamp joint element is coupled to the holding unit via a further linkage unit. The clamp joint element causes the front linkage to maintain a vertical orientation in every position of the medical-optical equipment independently of the position of the first and second parallel linkage pairs.

SUMMARY OF THE INVENTION

It is an object of the invention to provide a stand arrangement for a medical-optical instrument of the kind described above wherein an orientation of the front linkage does not change independently of the position of linkage units and wherein a good vibration decoupling is made possible for a medical-optical instrument accommodated on the stand arrangement.

The stand of the invention for a medical-optical instrument includes: a holding unit; a first link; a first rotational joint for pivotally supporting the first link on the holding unit; a second link having a forward section; a second rotational joint for rotatably connecting the second link to the first link; a take-up unit for accommodating the medical-optical instrument; a third rotational joint for carrying the take-up unit in the forward section; the take-up unit including a front link; a third link and a fourth link for connecting the front link to the second rotational joint; and, a toothed gear unit for coupling the holding unit and the fourth link so that a movement of the first link does not cause the orientation of the front link to change.

In this way, a stand arrangement is provided wherein a coupling mechanism of a holding unit and the fourth link can be accommodated in the first link. This makes possible a compact configuration of the stand arrangement and reduces the danger of squeezing which occurs during operation of the arrangement. A force surface contact with increased inner friction is produced in that a coupling of the holding unit and the fourth link takes place via toothed wheel gear assemblies. This causes vibrations of the holding unit (which vibrations can possibly come from the building) to be transmitted only very greatly attenuated to the medical-optical equipment accommodated on the arrangement.

According to a further feature of the invention, the toothed wheel gear assembly of the stand arrangement includes at least one toothed rod which coacts with a toothed element on the holding unit and a toothed element on the fourth link. It is also possible that the toothed gear assembly of the stand arrangement includes a gear element pivotally-movably journalled on the first link and this gear element has a first section with toothed elements which section coacts with the holding unit and which gear element is provided in a second section with toothed elements which section coacts with the fourth link. Furthermore, it is possible that the corresponding gear assembly includes a shaft which taps the movement of a toothed wheel on a toothed element on the holding unit and transmits the movement, by means of the toothed wheel, which coacts with a toothed element on the fourth link, thereto. In this way, it is possible to guide an arrangement for coupling the holding unit and the fourth link directly on the first link. In this way, a compact configuration is obtained and, with a corresponding sheathing, also easy cleanability of the stand arrangement is provided. The corresponding stand arrangement can easily be covered by a sterile drape for use in operating rooms.

According to another feature of the invention, the second link, the front link, the third link and the fourth link conjointly form a first parallel linkage. In this way, the second link can be configured to be cropped in order to increase the space for movement for a surgeon on the patient.

In a further embodiment of the invention, the second link is extended in a rearward section in order to form a second parallel linkage with a fifth link and a sixth link. In this way, space is provided for units for attenuating vibration on one of the links.

According to another feature of the invention, at least one balance weight is provided on the second parallel linkage. In this way, good mechanical balancing of the stand arrangement is made possible.

According to another feature of the invention, the holding unit of the stand arrangement is rotatable about an essentially vertically running axis. In this way, an optimal movability for a medical-optical instrument accommodated on the stand arrangement is achieved.

In a further embodiment of the invention, a unit for attenuating vibration is assigned to the toothed gear assembly of the stand arrangement. In this way, disturbing vibrations of a surgical microscope accommodated on the stand can be prevented. These vibrations impair a microscope image displayed to the viewer.

According to another feature of the invention, the arrangement for damping vibration includes a toothed element coupled to an eddy current brake unit. In this way, it is possible to dissipate vibrations, which occur on the stand arrangement, in the form of electric energy.

According to another feature of the invention, the arrangement for damping vibration includes a toothed element which is coupled to an electric motor. In this way, the conditions are provided that vibrations can be controllably countered which occur on the stand arrangement.

In a further embodiment of the invention, a control loop (open loop or closed loop) is coupled to an electric motor. Signals of an angle sensor and/or a distance sensor and/or a vibration sensor for detecting a movement in the gear assembly to be damped are supplied to the control loop. In this way, an active frequency selective vibration damping is made possible.

The stand arrangement can be configured as a floor stand as well as a ceiling stand.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
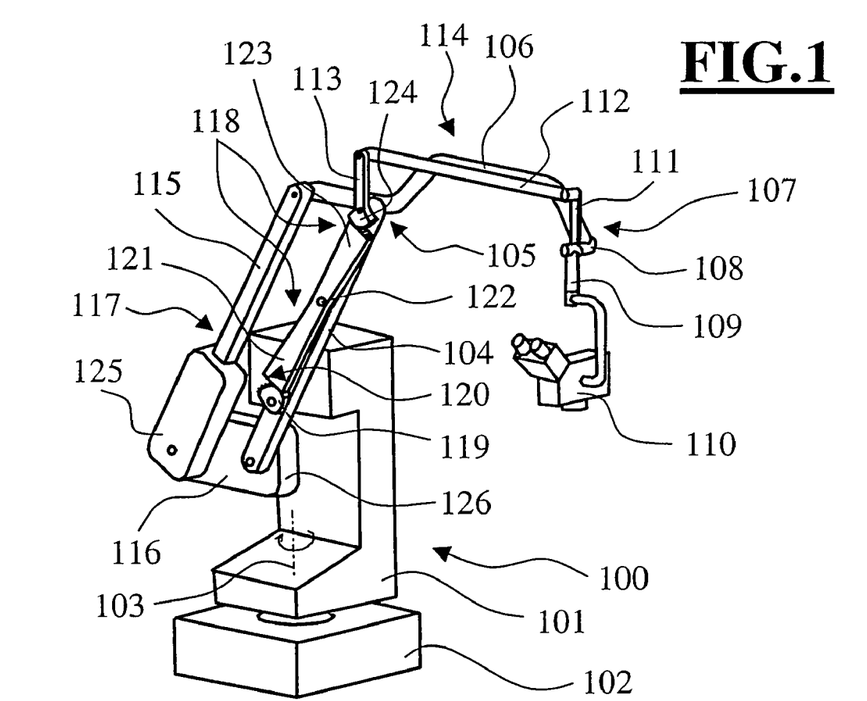
FIG. 1 is a perspective view of a first embodiment of the stand arrangement in a first position.

FIG. 1 shows a stand arrangement 100 having a stand console 101 as a holding unit. The holding unit is supported on a stand base 102 by means of a rotational joint and can be moved about a rotational axis 103. A first link 104 is pivotally-movably attached to the stand console 101 by means of a first rotational joint. A second link 106 is supported on this first link 104 by a second rotational joint 105. A take-up unit 109 is held by a rotational joint 108 on a forward end 107 of this second link 106. This take-up unit 109 carries a surgical microscope 110 as medical-optical equipment. The take-up unit 109 includes a front link 111 which forms a first parallel linkage assembly 114 together with a third link 112, a fourth link 113 and the second link 106. The second link 106 is configured so as to be extended on the end facing away from the take-up unit 109. The second link 106 forms a second parallel linkage assembly 117 together with a sixth link element 115 and a seventh link element 116.

The fourth link 113 acts as a coupling element and is coupled to the stand console 101 by means of a toothed gear unit 118 so that the orientation of the front link 111 does not change with a movement of the first link 104.

The toothed gear unit 118 has a first toothed element 119 which is rigidly connected to the stand console 101. This toothed element 119 meshes with teeth 120 which are formed on the end of a pivot lever element 121. This pivot lever element 121 is rotationally-movably supported on the first link 104 by a rotational shaft 122. Furthermore, a section having toothed elements 123 is provided at a second end of the pivot lever element 121. This section with toothed elements 123 operates together with a toothed surface 124 on the link 113.

The fifth link element 115 and the sixth link element 116 carry compensating weights 125 and 126. These compensating weights balance the weight of the links 112 and 106 as well as the medical-optical unit accommodated therein.

Figure 2:
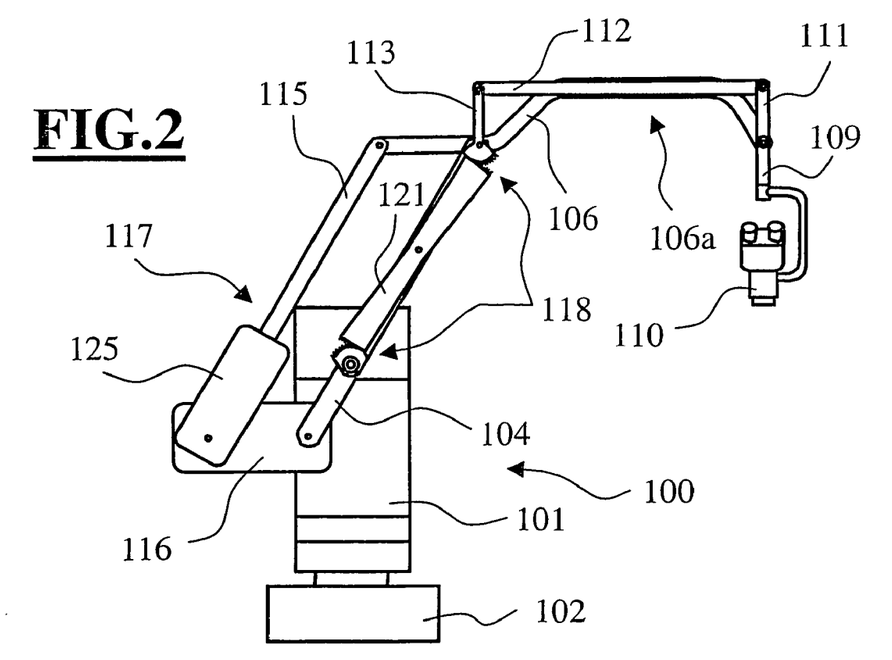
FIG. 2 is a side elevation view of the stand arrangement shown in FIG. 1.
Figure 3:
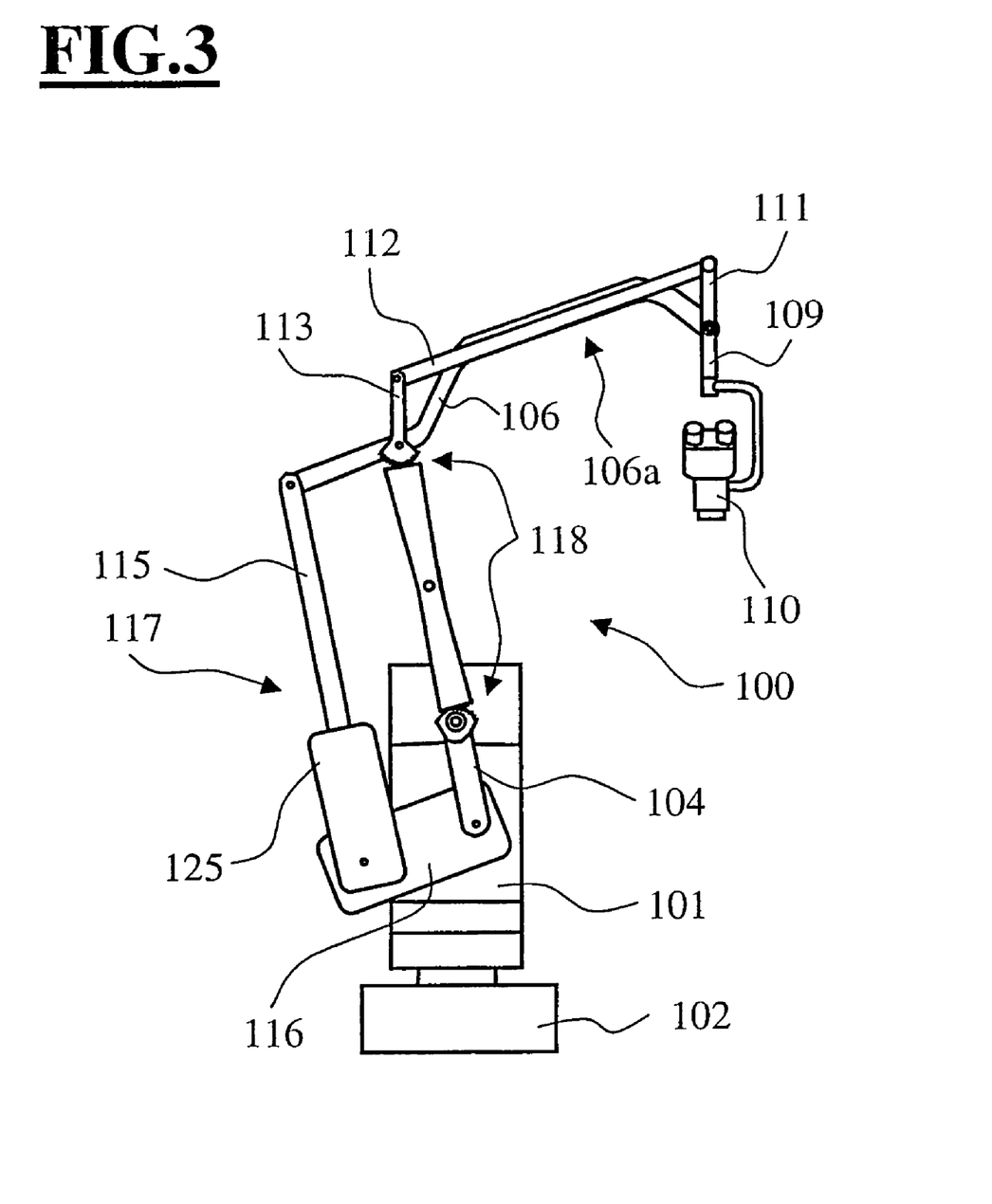
FIG. 3 is a side elevation view of the embodiment of FIG. 1 in a second position.

FIGS. 2 and 3 illustrate the operation of the toothed gear unit. The same reference numerals are used insofar as the component groups of the stand arrangement of FIGS. 2 and 3 are the same as in FIG. 1.

FIG. 2 shows a stand arrangement 100 having a far extending second link 106. This second link 106 is configured to be cropped in a region 106a. This makes possible that the operating surgeon has great freedom for the head. The toothed gear unit 118 couples the holding unit 101 and the fourth link 113 in such a manner that the front link 111 of the take-up unit 109 is always held vertically. Here it is noted that also other fixed orientations of the front link 111 can be obtained corresponding to other positions of the toothed gear unit 118.

In FIG. 3, the stand arrangement 100 is shown with the surgical microscope moved far upwardly. Here again, the toothed gear unit 118 ensures a vertical alignment of the front link 111 and the take-up unit 109.

Figure 4:
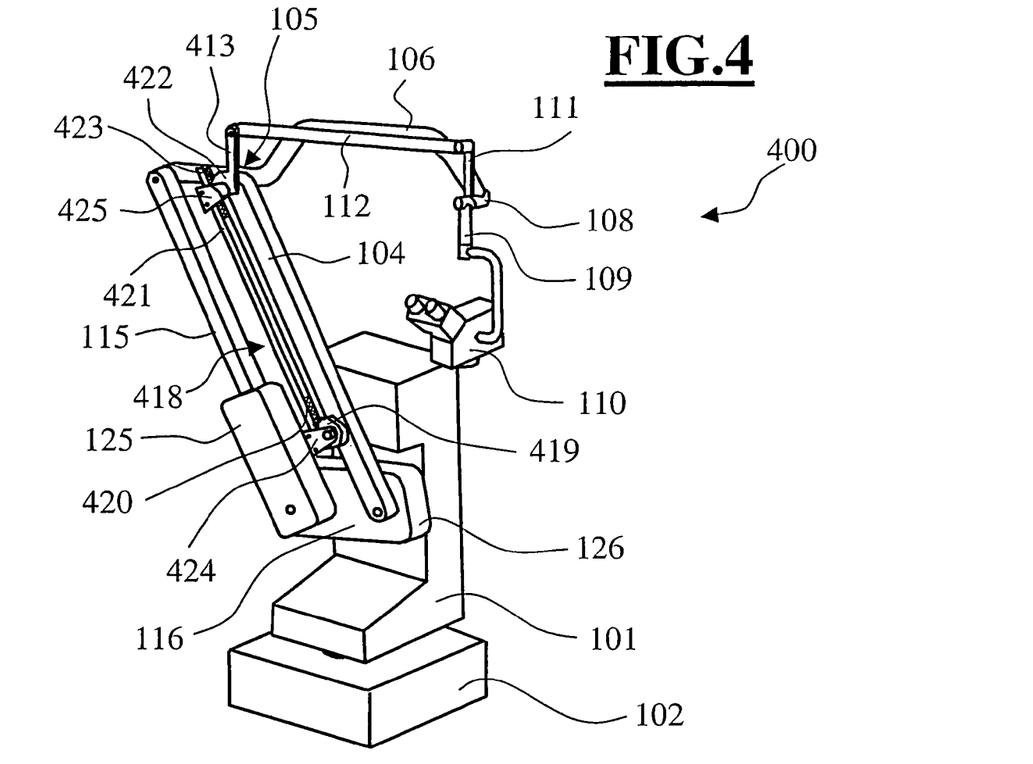
FIG. 4 is a perspective view of a second embodiment of the stand arrangement of the invention.

FIG. 4 shows a stand arrangement 400 whose configuration corresponds basically to that of the stand arrangement 100 of FIG. 1. Insofar as the stand arrangements 100 of FIG. 1 and 400 of FIG. 4 have identical component groups, the same reference numerals are used.

A rack mechanism 418 is provided for coupling the fourth link 413 of the stand arrangement 400 to the stand console 101. The rack mechanism 418 includes a first half pinion 419 which is rigidly connected to the console 101 and meshes with the toothed rod section 420 of the toothed rod or rack 421. A half pinion 422 is provided on the fourth link 413 and this half pinion is operatively connected to a toothed rod section 423 of the toothed rod or rack 421. The rack 421 is guided by means of holding elements 424 and 425 in the region of the half pinions 419 and 422. The adjustment of the half pinions 419 and 422 as well as the rack 421 is so selected that the front link 111 is always aligned vertically independently of the position of the link 104.

It is noted that basically also other adjustments of the half pinions and the rack can be selected in order to achieve another position of the front link 111.

Figure 5:
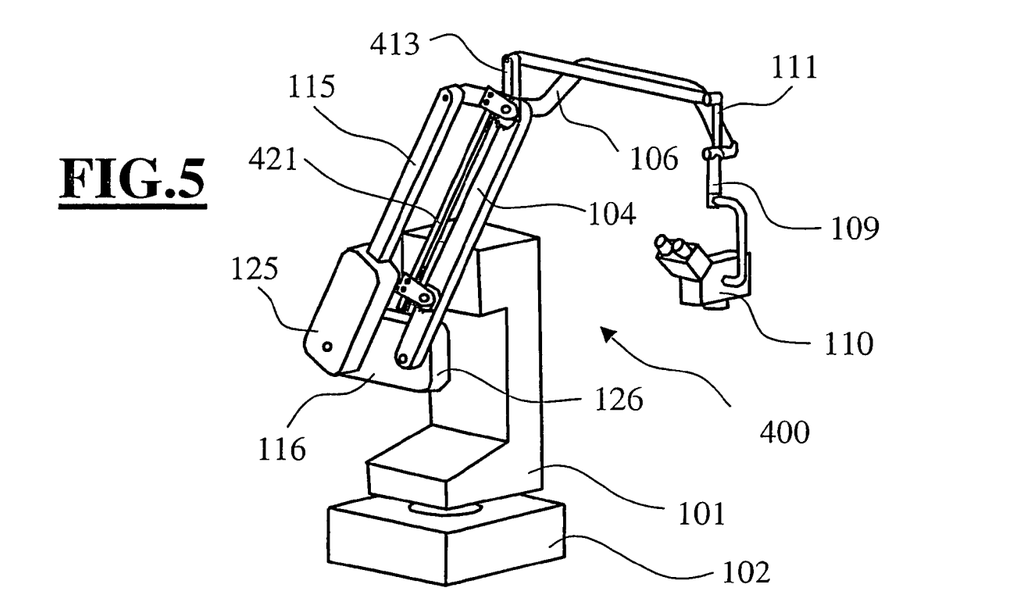
FIG. 5 is a side elevation view of the embodiment of FIG. 4 in a first position.

FIG. 5 shows a view of the stand arrangement 400 with a greatly extending third link 112 and illustrates the movement of the rack 421 relative to the link 104 which is required for reaching this position.

Figure 6:
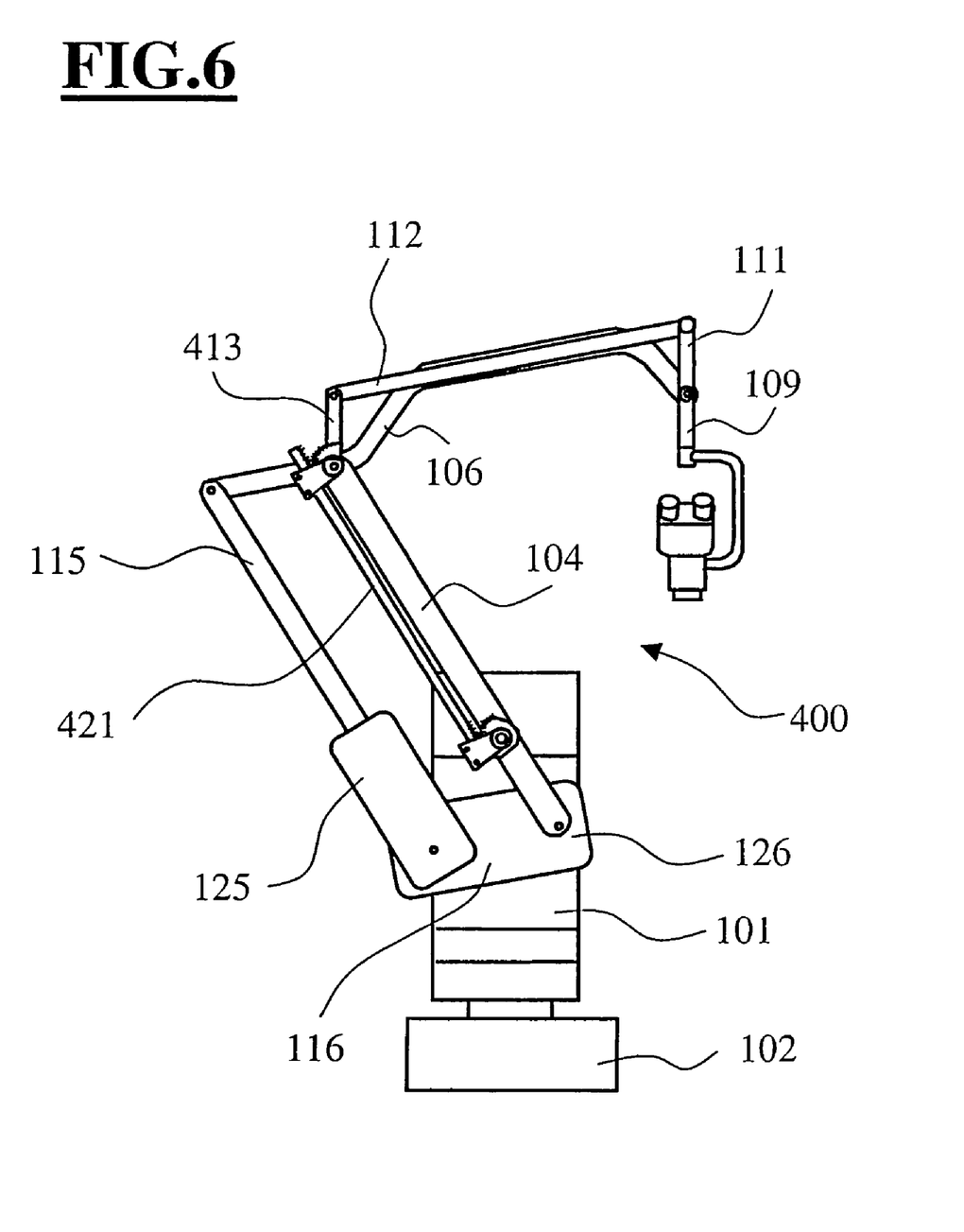
FIG. 6 is a side elevation view of the embodiment of FIG. 4 in a second position different from the first position.

Compared to the above, FIG. 6 shows a stand arrangement wherein the link 104 is pivoted toward the rearward end of the stand console 101. A vertical alignment of the third link 112 and therefore of the front link is obtained because of the movement of the rack 421.

Figures 7, 8:
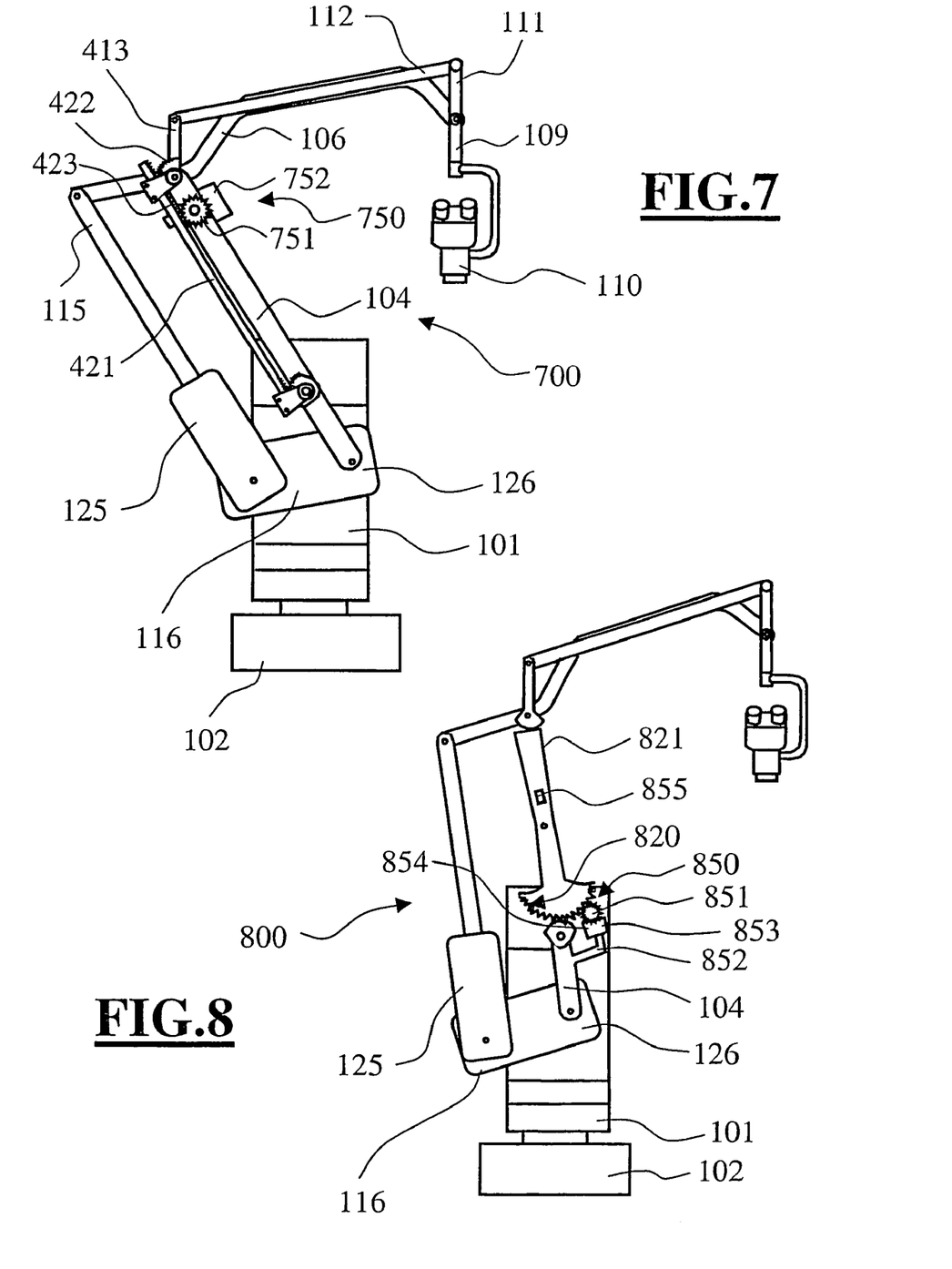
FIG. 7 is a third embodiment of the stand arrangement of the invention provided with a unit for damping vibration.
FIG. 8 is a side elevation view of a fourth embodiment having an alternate unit for actively damping vibration; and, FIG. 9 is a detail view of a fifth embodiment of the stand arrangement of the invention.

FIG. 7 shows a stand arrangement 700 whose basic configuration corresponds to the stand arrangement 400 of FIG. 4. Insofar as the component groups of the stand arrangement 700 are identical to the component groups of the stand arrangement 400 of FIG. 4, the same reference numerals are used.

A unit for vibration damping 750 is provided in the stand arrangement 700. This unit for vibration damping 750 includes a toothed wheel 751 as a toothed element which is rotatably supported on the link 104. This toothed wheel 751 is coupled to an eddy-current brake unit 752 and is in meshing engagement with the teeth in the rack section 423 of the toothed rod or rack 421. In the stand arrangement 700, vibration movements of the surgical microscope 110, which is carried on the take-up unit 109, are transmitted via links 111, 112 and 413 and via half pinion 422 to the rack 421 which is correspondingly moved back and forth thereby.

This back and forth movement of the rack 421 is tapped by means of a toothed wheel 751 and is braked by the eddy-current brake unit 752 which is operatively connected to the toothed wheel 751. In this way, occurring vibrations on the stand arrangement 700 are converted into electrical energy.

FIG. 8 shows a further stand arrangement 800 having a unit for vibration damping 850. The unit for vibration damping 850 is configured as a unit for active vibration damping. Basically, the configuration of the stand arrangement 800 of FIG. 8 corresponds to that of the stand arrangement 100 of FIG. 1. Insofar as the component groups of the particular stand arrangements are the same, they are used here.

The unit for active vibration damping 850 includes a toothed wheel 851 which is supported on a holding unit 852 which is fixedly connected to the link 104. This toothed wheel 851 is in meshing engagement with the teeth 820 of the pivot lever element 821. The toothed wheel 851 is driven by an electric motor 853. A control unit 854 is assigned to the electric motor 853 and signals of a vibration sensor 855 are supplied to the control unit 854. The vibration sensor 855 is mounted on the pivot lever element 821.

As in the stand arrangement described with respect to FIG. 7, a vibration movement of the surgical microscope 110, which is carried on the take-up unit 109, leads to a movement of the pivot lever element 821. This vibration movement is detected by the vibration sensor 855 which outputs corresponding signals to the control unit 854. This control unit 854 processes the signals of the vibration sensor 855 and outputs a countervibration signal to the electric motor 853. In this way, the electric motor 853 is so supplied with current that a vibration movement is countered in that the electric motor 853 suitably moves the toothed wheel 851.

In an alternate embodiment, an angle sensor for detecting an angular position of the pivot lever 821 or a distance detecting sensor for detecting a movement of the pivot lever 821 relative to the link 104 can be assigned to the control unit 854.

In lieu of assigning a closed loop control unit to the electric motor, an open loop control unit could be provided for driving the motor. Furthermore, and corresponding to the embodiment described with respect to FIG. 7, the toothed wheel 851 can also be coupled to an eddy-current brake. Then, the stand arrangement includes no active unit for damping vibration, rather, it includes a passive unit for damping vibration.

It is noted that in the stand arrangement 700 of FIG. 7, a corresponding drive having an electric motor and control unit for driving the toothed wheel 751 could be provided in lieu of the eddy-current brake as in the stand arrangement 800 of FIG. 8.

Figure 9:
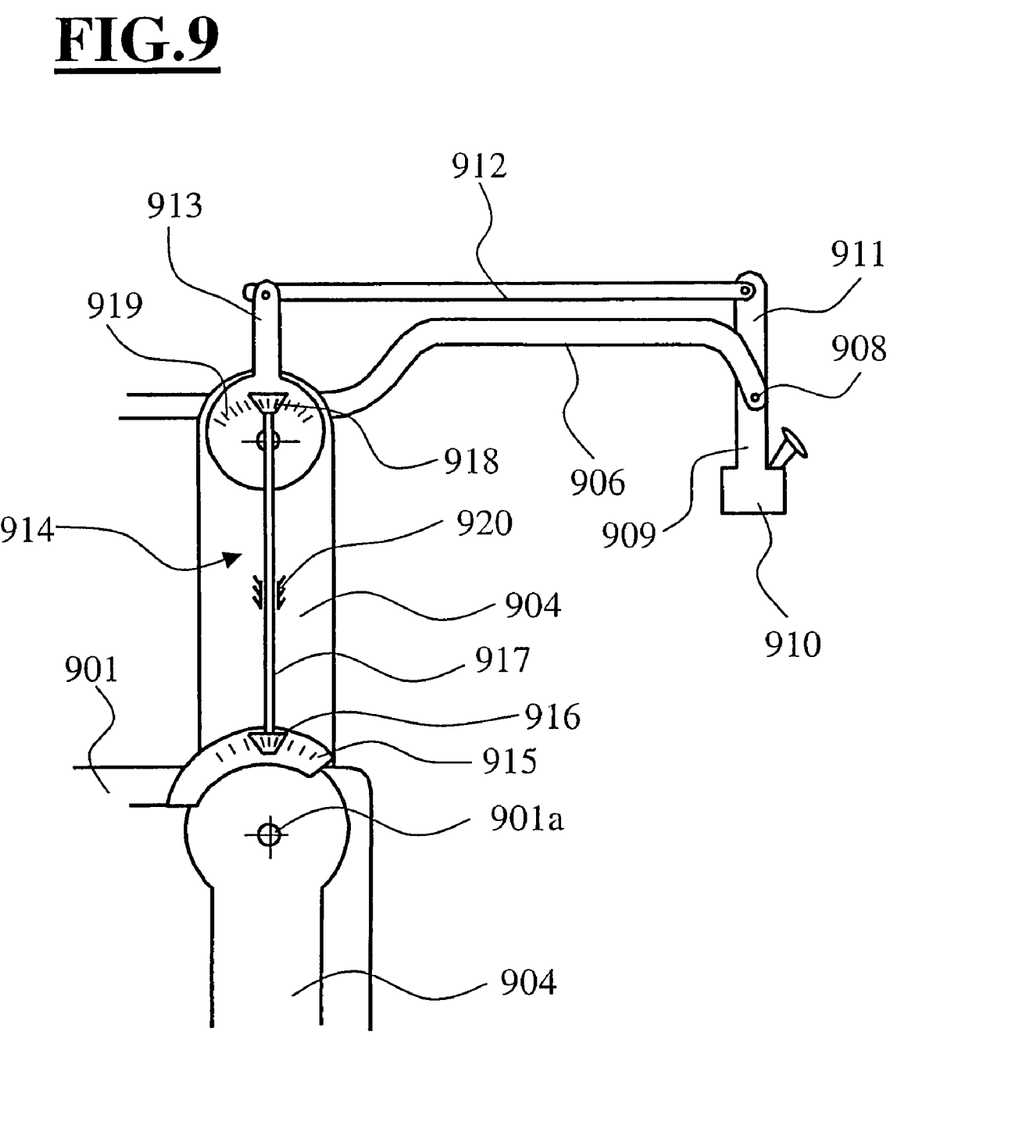

In FIG. 9, an alternate embodiment is described for a coupling mechanism of a stand console and a third link in a stand arrangement according to FIG. 1 or 4. FIG. 9 shows a stand arrangement having a stand console 901 configured as a holding unit. A first link 904 is fixed with a first rotational joint 901a to the stand console 901 so as to be pivotally movable. A second link 906 is rotatably connected to this first link 904 and the second link carries a take-up unit 909 in a rotational joint 908. The take-up unit 909 holds a surgical microscope 910 as medical-optical equipment and includes a front link 911. The front link 911 is connected to a link 913 via a link 912. In the stand arrangement of FIG. 9, the stand console 901 and the link 913 are coupled by means of a bevel gear unit 914. The bevel gear unit 914 has a set of teeth 915 rigidly connected to the stand console 901 and this set of teeth 915 meshes with a first bevel gear 916.

The bevel gear 916 is coupled to a second bevel gear 918 via a shaft 917. The second bevel gear 918 coacts with a set of teeth 919 which is configured on a second link 913. The shaft 917 is supported on the link 904 in a bearing 920. It is noted that the stand arrangement can be configured not only as a floor stand as shown in FIGS. 1 to 8, but also as a wall or ceiling stand.

It is understood that the foregoing description is that of the preferred embodiments of the invention and that various changes and modifications may be made thereto without departing from the spirit and scope of the invention as defined in the appended claims.

What is claimed is:

1. A stand for a medical-optical instrument, the stand comprising:
   a holding unit;
   a first link;
   a first rotational joint for pivotally supporting said first link on said holding unit;
   a second link having a forward section;
   a second rotational joint for rotatably connecting said second link to said first link;
   a take-up unit for accommodating said medical-optical instrument;
   a third rotational joint for carrying said take-up unit in said forward section;
   said take-up unit including a front link;
   a third link and a fourth link for connecting said front link to said second rotational joint; and,
   a toothed gear unit for coupling said holding unit and said fourth link so that a movement of said first link does not cause the orientation of said front link to change.

2. The stand of claim 1, wherein said toothed gear unit includes: a first toothed element on said holding unit and a second toothed element on said fourth link; and, at least one toothed rod for coacting with said first and second toothed elements.

3. The stand of claim 1, wherein said toothed gear unit includes:
   a gear element pivotally supported on said first link; and,
   said gear element including: a first section having toothed elements for coacting with said holding unit; and, a second section having toothed elements for coacting with said fourth link.

4. The stand of claim 1, wherein said toothed gear unit includes:
   a toothed element disposed on said holding unit;
   a first toothed wheel disposed on said toothed element;
   a shaft for tapping the movement of said first toothed wheel;
   said fourth link having a toothed element;
   a second toothed wheel coacting with said toothed element of said fourth link; and,
   said shaft coacting with said second toothed wheel to transmit said movement to said second toothed wheel.

5. The stand of claim 1, wherein said first link, said front link, said third link and said fourth link conjointly form a first parallel linkage.

6. The stand of claim 1, wherein said second link is lengthened with a rearward section and wherein said stand further comprises a fifth link and a sixth link; and, said rearward section, said fifth link and said sixth link conjointly define a second parallel linkage.

7. The stand of claim 6, further comprising at least one balancing weight disposed on said second parallel linkage.

8. The stand of claim 1, wherein said holding unit is rotatable about an axis which extends in a substantially vertical direction.

9. The stand of claim 1, further comprising a unit for damping vibrations and said unit for damping vibrations being assigned to said toothed gear unit.

10. The stand of claim 9, wherein said unit for damping vibrations includes a toothed element coupled to an eddy-current brake unit.

11. The stand of claim 10, wherein said unit for damping vibrations includes a toothed element coupled to an electric motor.

12. The stand of claim 11, further comprising a control loop connected to said electric motor and including at least one of the following: a vibration sensor, an angle sensor and a distance sensor for detecting a movement which is to be dampened.

13. The stand of claim 1, wherein said stand is configured as a floor stand.

14. The stand of claim 1, wherein said stand is configured as a ceiling stand.

* * * * *